United States Patent
Seko et al.

[11] Patent Number: 6,160,181
[45] Date of Patent: Dec. 12, 2000

[54] TETRAENE DERIVATIVE AND PROCESS FOR PRODUCING THE SAME

[75] Inventors: Shinzo Seko, Toyonaka; Naoto Konya, Takatsuki; Toshiya Takahashi, Ibaraki; Atsushi Furutani, Takatsuki, all of Japan

[73] Assignee: Sumitomo Chemical Company, Limited, Osaka, Japan

[21] Appl. No.: 09/382,699

[22] Filed: Aug. 25, 1999

[30] Foreign Application Priority Data

Sep. 1, 1998 [JP] Japan .................. 10-247143

[51] Int. Cl.$^7$ .................. C07C 315/04; C07C 317/08
[52] U.S. Cl. .................. 568/32; 568/28
[58] Field of Search .................. 568/27, 28, 32

[56] References Cited

U.S. PATENT DOCUMENTS

| | | | |
|---|---|---|---|
| 4,331,814 | 5/1982 | Chabardes et al. | 560/255 |
| 4,433,171 | 2/1984 | Chabardes et al. | 568/33 |
| 4,449,002 | 5/1984 | Sato et al. | 568/28 |
| 4,825,006 | 4/1989 | Otera et al. | 568/32 |
| 4,883,887 | 11/1989 | Bernhard et al. | 549/341 |
| 4,886,916 | 12/1989 | Onishi et al. | 569/34 |

OTHER PUBLICATIONS

J. B. Davis et al., "The Structures of Phytoene, Phytofluene, ζ–Carotene, and Neurosporene", *Proc. Chem. Soc.*, Jul. 1961, pp. 261–263.

Axel Nürrenbach et al., "Oxidation von Phosphor–Yliden mit Hydroperoxiden: Ein neuer und ergiebiger Weg zu symmetrischen Carotinoiden", *Liebigs Ann. Chem.*, 1977, pp. 1146–1159 with English Abstract.

*Chemical Abstracts*, vol. 50, pp. 15471–15472 1956.

*Helvetica Chimica Acta*, vol. 39, No. 54, 1956, pp. 463–473.

*Primary Examiner*—Johann Richter
*Assistant Examiner*—Jean F Vollano
*Attorney, Agent, or Firm*—Sughrue, Mion, Zinn, Macpeak & Seas, PLLC

[57] ABSTRACT

A tetraene derivative of the formula (1):

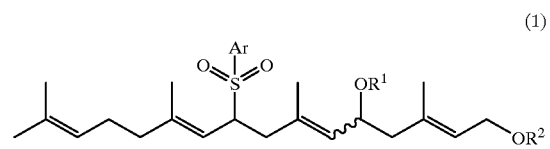

wherein Ar represents an aryl group which may be optionally substituted with at least one substituent, and $R^1$ and $R^2$ are identical or different and represent a hydrogen atom, a lower alkyl group or a protective group of a hydroxyl group; synthesis methods therefor and synthesis methods using the same.

16 Claims, No Drawings

TETRAENE DERIVATIVE AND PROCESS FOR PRODUCING THE SAME

BACKGROUND OF THE INVENTION

1. Field of the Invention

The present invention relates to tetraene derivatives useful as intermediates to carotenoids, such as lycopene and its analogues, important in the fields of pharmaceuticals, feed additives and food additives, and concerns their manufacturing methods.

2. Related Art

Heretofore, as a synthesizing method of lycopene which is a symmetrical C40 compound, there have been known, for example, a method in which two molecules of a C15 compound and one molecule of a C10 compound are coupled, a method in which two molecules of a C10 compound and one molecule of a C20 compound are coupled (see, for example, Pure & Appl. Chem., Vol. 69, 2039 (1997), Helv. Chim. Acta, Vol. 39, 463 (1956), etc.), and a method in which two molecules of a C8 compound and one molecule of a C24 compound are coupled (see, for example, DE 2554924, etc.). It is, however, difficult to say that these methods are completely suitable because they require one to synthesize two types of compounds separately, which are different in their number of carbon atoms and molecular structure. On the other hand, a method in which two molecules of a C20 compound are coupled, which has been reported in Proc. Chem. Soc., 261 (1961), Liebigs Ann. Chem., 1146 (1977), etc., is thought to be a preferable manner of reaction. However, since it requires multiple steps to synthesize the C20 compound, it does not necessarily have much industrial practicality.

SUMMARY OF THE INVENTION

To solve the above-mentioned problems, the present inventors have intensively studied to develop C20 compounds that are useful in the synthesis of C40 compounds such as lycopene, industrially advantageous processes utilizing the same, and have thus accomplished the present invention.

The present invention provides:

1. a novel tetraene derivative of the formula (1):

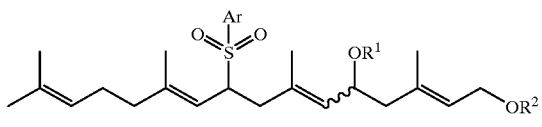

(1)

wherein Ar represents an aryl group which may be optionally substituted with at least one substituent, $R^1$ and $R^2$ are identical or different and represent a hydrogen atom, a lower alkyl group or a protective group of a hydroxyl group;

2. a process for producing a tetraene derivative of the formula (6):

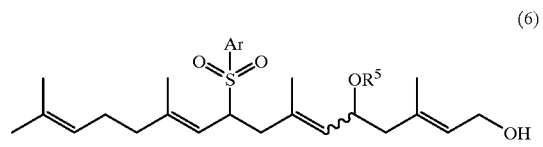

(6)

wherein Ar has the same meaning as defined above and $R^5$ represents a lower alkyl group, the process comprising:

reacting a sulfone of the formula (2):

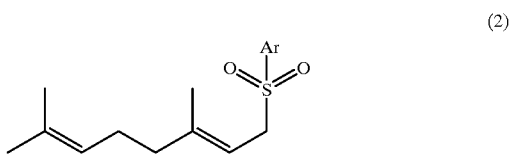

(2)

wherein Ar has the same meaning as defined above, with a halohydrin derivative of the formula (3):

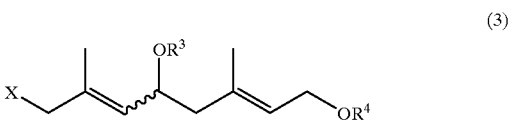

(3)

wherein X represents a halogen atom and $R^3$ and $R^4$ are identical or different and represent a protective group of a hydroxyl group, in the presence of a base to obtain a tetraene derivative of the formula (4):

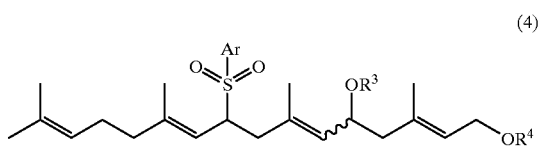

(4)

wherein Ar, $R^3$ and $R^4$ have the same meaning as defined above, subjecting the tetraene derivative of the formula (4) to a deprotection reaction to obtain a tetraene derivative of the formula (5):

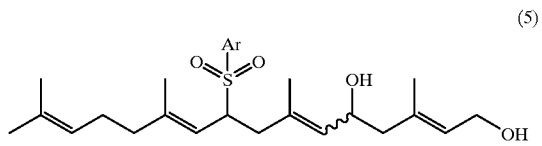

(5)

wherein Ar has the same meaning as defined above, and reacting the tetraene derivative of the formula (5) with a lower alcohol in the presence of an acid catalyst;

3. a process for producing a tetraene derivative of the formula (6):

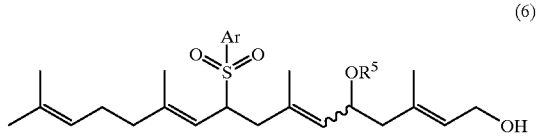

(6)

wherein Ar represents an aryl group which may be optionally substituted with at least one substituent, and $R^5$ represents a lower alkyl group, the process comprising reacting the tetraene derivative of the formula (5) as defined above with a lower alcohol in the presence of an acid catalyst; and 4. a process for producing a tetraene derivative of the formula (7):

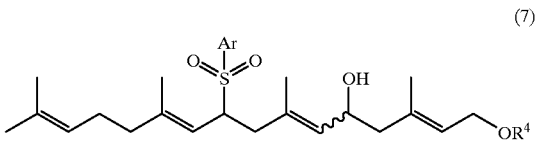

(7)

wherein Ar and $R^4$ have the same meaning as defined above, the process comprising:

reacting the tetraene derivative of the formula (5) with a protective agent in the presence of a phase-transfer catalyst and a base.

DETAILED DESCRIPTION OF THE INVENTION

The present invention is described in detail below.

Examples of the protective groups of a hydroxyl group in the substituents $R^1$, $R^2$, $R^3$ and $R^4$ in the tetraene derivatives (1), (4), (7) and the halohydrin derivative (3) of the present invention include, but are not limited to the following:

acyl groups such as acetyl, pivaloyl, benzoyl, p-nitrobenzoyl and the like, silyl groups such as trimethylsilyl, t-butyldimethylsilyl, t-butyldiphenylsilyl and the like, alkoxymethyl groups such as tetrahydropyranyl, methoxymethyl, methoxyethoxymethyl, 1-ethoxyethyl and the like, a benzyl group, a p-methoxybenzyl group, a trityl group, and the like, a t-butyl group and the like, a benzyloxycarbonyl group a 2,2,2-trichloroethoxycarbonyl group, an allyloxycarbonyl group and the like, As examples of the protective groups of the hydroxyl group and of protective agents described below, "Protective Groups in Organic Synthesis, Greene and Wuts, 2nd Edition (1992), John Wiley & Sons, Inc", can be referred to, the whole disclosure of which is incorporated herein by reference.

Examples of the lower alkyl groups in the substituents $R^1$, $R^2$ and $R^5$ in the tetraene derivatives (1) and (6) include linear or branched C1 to C4 alkyl groups, specifically methyl, ethyl, n-propyl, isopropyl, n-butyl, isobutyl, t-butyl and the like.

The substituent X in the halohydrin derivative (3) represents a halogen atom such as a chlorine atom, a bromine atom, an iodine atom, etc.

The substituents Ar in the sulfone (2) and the tetraene derivatives (1), (4), (5), (6) and (7) represent aryl groups which may be optionally substituted with at least one substituent. Examples of the aryl groups include a phenyl group, a naphthyl group, etc. The optional at least one substituent on the Ar groups may be selected from C1 to C6 alkyl groups, C1 to C6 alkoxy groups, halogen atoms, a nitro group, etc. Specific examples thereof include phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, p-nitrophenyl, etc.

In the present specification, chemical formulae having a single bond depicted by "〰", means that the compounds represented by the formulae may be an E-isomer, a Z-isomer, or a mixture thereof.

The tetraene derivative (4) of the present invention can be obtained by reacting the sulfone of the formula (2) with the halohydrin derivative of the formula (3) in the presence of a base.

Examples of the base to be used in the above reaction include alkyllithiums, Grignard reagents, alkali metal hydroxides, alkaline earth metal hydroxides, alkali metal hydrides, alkaline earth metal hydrides, alkali metal alkoxides and alkaline earth metal alkoxides. Specific examples thereof include n-butyllithium, s-butyllithium, t-butyllithium, methylmagnesium bromide, methylmagnesium chloride, ethylmagnesium bromide, ethylmagnesium chloride, sodium hydroxide, potassium hydroxide, magnesium hydroxide, sodium hydride, potassium hydride, sodium methoxide, potassium methoxide, magnesium methoxide, sodium t-butoxide, potassium t-butoxide, etc. The amount of the base used is usually about 0.1–4 moles per mol of the sulfone of the formula (2).

In the above reaction, a phase-transfer catalyst may be preferably employed in order to accelerate the reaction.

Examples of the phase-transfer catalyst used include quaternary ammonium salts, quaternary phosphonium salts, sulfonium salts, etc.

Examples of the quaternary ammonium salts include tetramethylammonium chloride, tetraethylammonium chloride, tetrapropylammonium chloride, tetrabutylammonium chloride, tetrapentylammonium chloride, tetrahexylammonium chloride, tetraheptylammonium chloride, tetraoctylammonium chloride, tetrahexadecylammonium chloride, tetraoctadecylammonium chloride, benzyltrimethylammonium chloride, benzyltriethylammonium chloride, benzyltributylammonium chloride, 1-methylpyridinium chloride, 1-hexadecylpyridinium chloride, 1,4-dimethylpyridinium chloride, trimethylcyclopropylammonium chloride, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, tetraoctylammonium bromide, tetrahexadecylammonium bromide, tetraoctadecylammonium bromide, benzyltrimethylammonium bromide, benzyltriethylammonium bromide, benzyltributylammonium bromide, 1-methylpyridinium bromide, 1-hexadecylpyridinium bromide, 1,4-dimethylpyridinium bromide, trimethylcyclopropylammonium bromide, tetramethylammonium iodide, tetrabutylammonium iodide, tetraoctylammonium iodide, t-butylethyldimethylammonium iodide, tetradecyltrimethylammonium iodide, hexadecyltrimethylammonium iodide, octadecyltrimethylammonium iodide, benzyltrimethylammonium iodide, benzyltriethylammonium iodide, benzyltributylammonium iodide, etc.

Examples of the quaternary phosphonium salts include tributylmethylphosphonium chloride, triethylmethylphosphonium chloride, methyltriphenoxyphosphonium chloride, butyltriphenylphosphonium chloride, tetrabutylphosphonium chloride, benzyltriphenylphosphonium chloride, hexadecyltrimethylphosphonium chloride, hexadecyltributylphosphonium chloride, hexadecyldimethylethylphosphonium chloride, tetraphenylphosphonium chloride, tributylmethylphosphonium bromide, triethylmethylphosphonium bromide, methyltriphenoxyphosphonium bromide, butyltriphenylphosphonium bromide, tetrabutylphosphonium bromide, benzyltriphenylphosphonium bromide, hexadecyltrimethylphosphonium bromide, hexadecyltributylphosphonium bromide, hexadecyldimethylethylphosphonium bromide, tetraphenylphosphonium bromide, tributylmethylphosphonium iodide, triethylmethylphosphonium iodide, methyltriphenoxyphosphonium iodide, butyltriphenylphosphonium iodide, tetrabutylphosphonium iodide, benzyltriphenylphosphonium iodide, hexadecyltrimethylpbosphonium iodide, etc.

Examples of the sulfonium salts include dibutylmethylsulfonium chloride, trimethylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide, triethylsulfonium iodide, etc.

The amount of the phase-transfer catalyst used is usually about 0.01– 0.2 mol, preferably about 0.02–0.1 mol per mol of the sulfone (2).

In the above reaction, an organic solvent is usually used. Examples of the solvent include ether solvents such as diethyl ether, tetrahydrofuran, dimethoxyethane, 1,4-dioxane and anisole, aprotic polar solvents such as N,N-dimethylformamide, dimethyl sulfoxide, N,N-dimethylacetamide, sulfolane and hexamethylphosphoric triamide, and hydrocarbon solvents such as n-hexane, cyclohexane, n-pentane, n-heptane, benzene, toluene and xylene.

The reaction temperature is usually in the range of from −78° C. to the boiling point of the solvent used. Although the reaction time varies depending on the types of the base and the catalyst used in the reaction and on the reaction temperature, it usually falls within the range of 1 hour to 24 hours.

After the reaction, the tetraene derivative of the formula (4) can be obtained by a conventional method such as extraction, phase separation, washing and/or evaporation, and may be further purified by various types of conventional chromatography known in the art, etc., if necessary.

The halohydrin derivative of the formula (3), may be an E-isomer, a Z-isomer, or a mixture thereof. Furthermore, it may also be a racemic mixture or an optically active substance.

The sulfone of the formula (2) and the halohydrin derivative of the formula (3), can be readily synthesized in the route shown in Scheme 1 from linalool or geraniol, which are commercially available at relatively low costs. A synthetic method of sulfone (2) is disclosed in J. Org. Chem., Vol. 39, 2135 (1974). A synthetic method of halohydrin derivative of the formula (3) is disclosed in EP900785A.

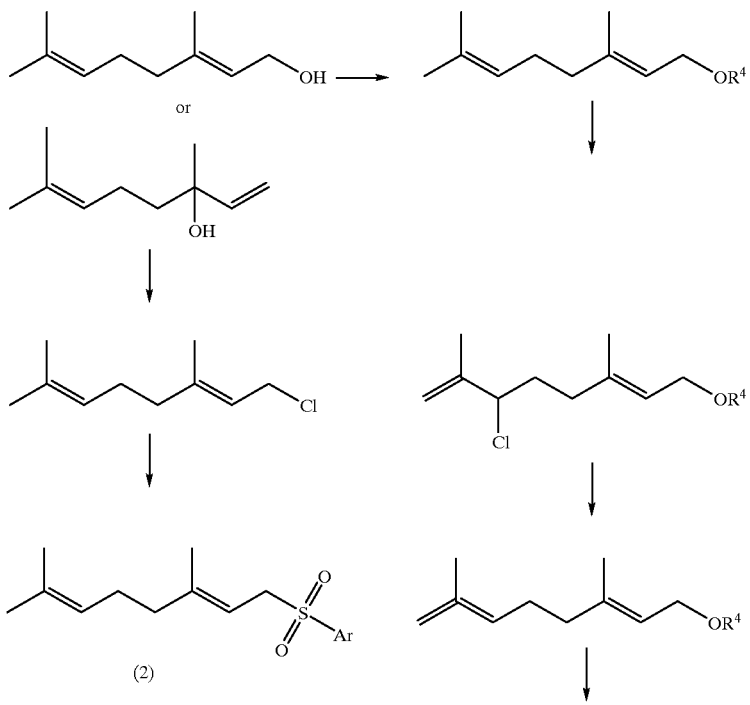

Scheme 1

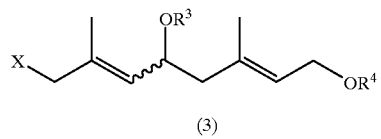

(3)

The tetraene derivative (5) can be obtained by deprotecting the protective group of hydroxyl groups of the tetraene derivative (4) by a conventional method suitable for the protective group.

The tetraene derivative (6) can be obtained by reacting an acid catalyst with the tetraene derivative (5) in a lower alcohol. In this reaction, a secondary hydroxyl group can be alkylated selectively.

The acid catalyst used in the above reaction may be Lewis acids, Brønsted acids, heteropolyacids, acidic ion-exchange resins, or the like. Specific examples of the Lewis acids include tin(II) chloride, tin(IV) chloride, zinc chloride, iron (III) chloride, boron trifluoride ether complex, rare earth metal triflates(trifluoromethanesulfonates), etc. Examples of the Brønsted acids include hydrobromic acid, hydrochloric acid, sulfuric acid, p-toluenesulfonic acid, benzenesulfonic acid, methanesulfonic acid, benzoic acid, triphenylphosphine hydrobromide, pyridine hydrochloride, etc. An example of the acidic ion-exchange resin is one of the strongly acidic types which has a sulfonic acid group on its end.

The amount of the acidic catalyst used is usually about 0.01–1 mol per mol of the tetraene derivative (5).

Examples of the lower alcohol used as a solvent in the above reaction include methanol, ethanol, n-propanol, isopropanol, n-butanol, isobutanol, t-butanol, etc. Methanol, ethanol or isopropanol is preferably used.

The reaction temperature is usually in the range of from −78° C. to the boiling point of the solvent used, preferably in the range of from −10° C. to 50° C. Although the reaction time varies depending on the type of the acidic catalyst used in the reaction and on the reaction temperature, it usually falls within the range of about 1 hour to 24 hours.

After the reaction, the tetraene derivative (6) can be obtained by a conventional method such as phase separation, washing and/or evaporation, and may be further purified by various types of conventional chromatography known in the art, etc., if necessary.

The tetraene derivative (7) can be obtained by reacting the tetraene derivative (5) with a protective agent in the presence of a phase-transfer catalyst and a base.

The protective agent used in the above reaction may be halides represented by R'Y or acid anhydrides. Preferable halides are acyl halides. Examples of R' in the halides of R'Y include acyl groups such as acetyl, pivaloyl, benzoyl and p-nitrobenzoyl, silyl groups such as trimethylsilyl, t-butyldimethylsilyl and t-butylphenylsilyl, alkoxymethyl groups such as methoxymethyl, a benzyl group, a p-methoxybenzyl group, a trityl group, a benzyloxycarbonyl group, a 2,2,2-trichloroethoxycarbonyl group, an allyloxycarbonyl group, etc. Examples of Y in the halides of R'Y include halogen atoms such as chlorine, bromine, iodine, etc.

Examples of the halides include acetyl chloride, pivaloyl chloride, benzoyl chloride, p-nitrobenzoyl chloride, trimethylsilyl chloride, t-butyldimethylsilyl chloride, methoxymethyl chloride, benzyl chloride, trityl chloride, benzyloxycarbonyl chloride, allyloxycarbonyl chloride, etc. and corresponding bromides and iodides. Preferred is acetyl chloride.

Examples of the acid anhydrides include acetic anhydride, propionic anhydride, butyric anhydride, etc. Preferred is acetic anhydride.

The amount of the protective agent used is usually about 0.1–1.1 mol per mol of the tetraene derivative of the formula (5).

Examples of the base used in the above reaction include organic amine bases and inorganic bases. Preferred are the inorganic bases. Examples of the organic amine bases include pyridine, 4-dimethylaminopyridine, 3-ethyl-4-methylpyridine, 5-ethyl-2-methylpyridine, imidazole, 2-methylimidazole, 3-methylimidazole, 2-ethyl-4-methylimidazole, DBU(1,8-diazabicyclo[5.4.0]undec-7-ene), DBN(1,5-diazabicyclo[4.3.0]non-5-ene), trimethylamine, triethylamine, diisopropylethylamine, diethylmethylamine, t-butyldimethylamine, diisopropylamine, etc. Examples of the inorganic bases include hydroxides of alkali metals or alkaline earth metals, carbonates of alkali metals or alkaline earth metals, hydrogencarbonates of alkali metals or alkaline earth metals, etc. Specific examples include sodium hydroxide, potassium hydroxide, magnesium hydroxide, calcium hydroxide, sodium carbonate, potassium carbonate, calcium carbonate, sodium hydrogencarbonate, potassium hydrogencarbonate, etc. These inorganic bases are preferably in the form of fine powders.

The amount of the base used is usually about 1–5 moles per mol of the tetraene derivative of the formula (5).

Examples of the phase-transfer catalyst used in the above reaction may be identical with those exemplified in the reaction of the sulfone (2) with the halohydrin derivative (3) described above.

The amount of the phase-transfer catalyst is usually about 0.01–0.2 mol, preferably about 0.02–0.1 mol, per mol of the tetraene derivative of the formula (5).

In the above reaction, an organic solvent is usually used. Examples of the solvent include hydrocarbon solvents such as n-hexane, cyclohexane, n-pentane, n-heptane, benzene, toluene and xylene, ether solvents such as diethyl ether, tetrahydrofuran, dimethoxyethane, 1,4-dioxane and anisole, halogen-containing solvents such as chloroform, dichloromethane, 1,2-dichloroethane, monochlorobenzene and o-dichlorobenzene, aprotic polar solvents such as N,N-dimethylformamide, dimethyl sulfoxide, N,N-dimethylacetamide and hexamethylphosphoric triamide.

The reaction temperature is usually in the range of from −78° C. to the boiling point of the solvent used, preferably in the range of from 0° C. to 30° C. Although the reaction time varies depending on the types of the base and the catalyst used in the reaction and on the reaction temperature, it usually falls within the range of about 1 hour to 24 hours.

After the reaction, the tetraene derivative (7) can be obtained by a conventional method such as extraction, phase separation, washing and/or evaporation, and may be further purified by various types of chromatography known in the art, etc., if necessary.

The tetraene derivative (1), which is the novel C20 compound of the present invention, is useful on the ground that it can be synthesized industrially advantageously from readily available C10 compounds such as linalool and geraniol, and that it can be readily converted into C40 compounds such as lycopene by converting its functional group followed by coupling two molecules of the resulting compounds.

EXAMPLES

The present invention is further explained by the following examples, but the invention is not limited to the examples.

Example 1

In 20 ml of tetrahydrofuran (THF), 0.53 g (1.8 mmol) of geranyl p-tolylsulfone (I) was dissolved and cooled to −60° C. 1.13 ml of 1.6 M solution of n-butyllithium (1.8 mmol) in hexane was added dropwise at that temperature, and after stirring for three hours, a solution (5 ml) of 0.3 g (0.9 mmol) of a halohydrin derivative (II) in THF was added dropwise over one hour at the same temperature. After stirring at that temperature for three hours, the reaction mixture was quenched with a saturated aqueous ammonium chloride solution, and extracted with ether. The organic layer obtained was washed with a saturated brine, dried over anhydrous magnesium sulfate, and the solvent was evaporated to yield a crude product. The resulting crude product was purified by silica gel chromatography to provide a tetraene derivative (III) in a yield of 49% in the form of pale yellow oil.

$^1$H-NMR δ (CDCl$_3$) 1.60 (3H, s), 1.67 (3H, s), 1.70 (3H, s), 1.57–1.76 (2H, m), 1.93 (3H, s), 190–2.36 (5H, m), 2.00 (3H, s), 2.04 (3H, s), 2.44 (3H, s), 282–2.95 (1H, m), 3.79–3.86 (1H, m), 4.53 (2H, d, J=7 Hz), 4.81–5.15 (3H, m), 5.33 (1H, m), 5.57 (1H, m), 7.29 (2H, d, J=8 Hz), 7.67 (2H, d, J=8 Hz)

Example 2

In a mixed solvent of 16 ml of THF and 4 ml of hexamethylphosphoric triamide, 0.53 g (1.8 mmol) of geranyl p-tolylsulfone (I) was dissolved, and at room temperature 0.072 g (1.8 mmol) of sodium hydroxide and 0.058 g (0.18 mmol) of tetra-n-butylammonium bromide were added, and then stirred for three hours at 40° C.–45° C. After that, the mixture was cooled to −60° C., and a solution (5 ml) of 0.3 g (0.9 mmol) of the halohydrin derivative (II) in THF was added dropwise over one hour. After stirring at that temperature for five hours, the temperature was elevated to 60° C. and the mixture was stirred at that temperature for five hours. After the reaction, the reaction mixture was quenched with a saturated aqueous ammonium chloride solution, and extracted with ether. The organic layer obtained was washed with a saturated brine, dried over anhydrous magnesium sulfate, and the solvent was evaporated to yield a crude product. The resulting crude product was purified by silica gel chromatography to provide the tetraene derivative (III) in a yield of 51% in the form of pale yellow oil.

Example 3

2.93 g (10 mmol) of geranyl p-tolylsulfone (I) and 1.55 g (13.8 mmol) of potassium t-butoxide were cooled to −60° C., and 15 ml of N,N-dimethylformamide (DMF) was added and stirred at that temperature for 30 minutes. To the mixture was added dropwise a solution (10 ml) of 3.37 g (10.1 mmol) of the halohydrin derivative (II) in DMF at the same temperature. After stirring at that temperature for two hours, the reaction mixture was quenched with a saturated aqueous ammonium chloride solution, and extracted with ethyl acetate. The organic layer obtained was washed with water and a saturated brine, dried over anhydrous magnesium sulfate, and the solvent was evaporated to yield a crude product. The resulting crude product was purified by silica gel chromatography to provide the tetraene derivative (III) in a yield of 70% in the form of pale yellow oil.

Example 4

In 10 ml of methanol, 2.55 g (4.68 mmol) of the tetraene derivative (III) was dissolved, and 1.12 g (5.62 mmol) of a 20% aqueous sodium hydroxide solution was added and stirred at room temperature for two hours. After the reaction, the reaction mixture was quenched with a saturated aqueous ammonium chloride solution, and extracted with ether. The organic layer obtained was washed with a saturated brine, dried over anhydrous magnesium sulfate, and the solvent was evaporated to yield a crude product. The resulting crude product was purified by silica gel chromatography to provide a tetraene derivative (IV) in a yield of 95% in the form of pale yellow oil.

$^1$H-NMR δ (CDCl$_3$) 1.55–1.71 (4H, m), 1.56 (3H, s), 1.62 (3H, s), 1.68 (6H, s), 1.80–1.94 (2H, m), 1.93 (3H, s), 2.25–2.41 (1H, m), 2.44 (3H, s), 2.82–2.95 (1H, m), 3.42 (1H, br s), 3.89 (1H, t, J=7 Hz), 4.04–4.08 (2H, m), 4.38–4.47 (1H, m), 4.69 (1s), 4.90 (1H, d, J=7 Hz), 4.98 (1H, br), 5.15–5.27 (1H, m), 5.45–5.51 (1H, t, J=7 Hz), 7.29 (2H, d, J=8 Hz), 7.67 (2H, d, J=8 Hz)

Example 5

In 28 ml of methanol, 2.50 g (5.43 mmol) of the tetraene derivative (IV) was dissolved, and 55 mg (0.54 mmol) of 96% concentrated sulfuric acid was added and stirred at room temperature for 24 hours. After the reaction, the reaction mixture was quenched with a saturated aqueous sodium hydrogencarbonate solution, and extracted with ether. The organic layer obtained was washed with a saturated brine, dried over anhydrous magnesium sulfate, and the solvent was evaporated to yield a crude product. The resulting crude product was purified by silica gel chromatography to provide a tetraene derivative (V) in a yield of 77% in the form of pale yellow oil.

$^1$H-NMR δ (CDCl$_3$) 1.18–1.23 (3H, m), 1.59 (3H, s), 1.67 (6H, br), 1.57–1.68 (2H, m), 1.93 (3H, br), 1.80–2.40 (3H, m), 2.41 (3H, s), 2.45–3.00 (3H, m), 3.11–3.23 (3H, m), 3.75–4.20 (4H, m), 4.80–5.18 (3H, m), 5.30–5.60 (1H, m), 7.20–7.35 (2H, m), 7.60–7.75 (2H, m)

Example 6

In 20 ml of hexane, 60 mg (0.13 mmol) of the tetraene derivative (IV) was dissolved, and 3.4 mg (0.013 mmol) of n-dodecyltrimethylammonium chloride and 14 mg (0.13 mmol) of sodium carbonate were added. And then 14 mg (0.13 mmol) of acetic anhydride was added and stirred at room temperature for 20 hours. After the reaction, the reaction mixture was quenched with water, and extracted with ether. The organic layer obtained was washed with an aqueous ammonium chloride solution and a saturated brine, dried over anhydrous magnesium sulfate, and the solvent was evaporated to yield a crude product. The resulting crude product was purified by silica gel chromatography to provide a tetraene derivative (VI) in a yield of 92% in the form of pale yellow oil.

$^1$H-NMR δ (CDCl$_3$) 1.57 (3H, s), 1.60 (3H, s), 1.66 (3H, s), 1.69 (3H, s), 1.92 (3H, s), 2.01 (3H, s), 2.05–2.28 (6H, m), 2.44 (3H, s), 2.85–2.92 (2H, d, J=8 Hz), 3.89 (1H, t, J=7 Hz), 4.38–4.49 (1H, m), 4.57 (2H, d, J=7 Hz), 4.89 (1H, d, J=8 Hz), 5.04 (1H, br, s), 5.15 (1H, d, J=8 Hz), 5.40 (1H, t, J=7 Hz), 7.31 (2H, d, J=8 Hz), 7.79 (2H, d, J=8 Hz)

The following are the structural formulae of the compounds (I)–(VI) of the Examples.

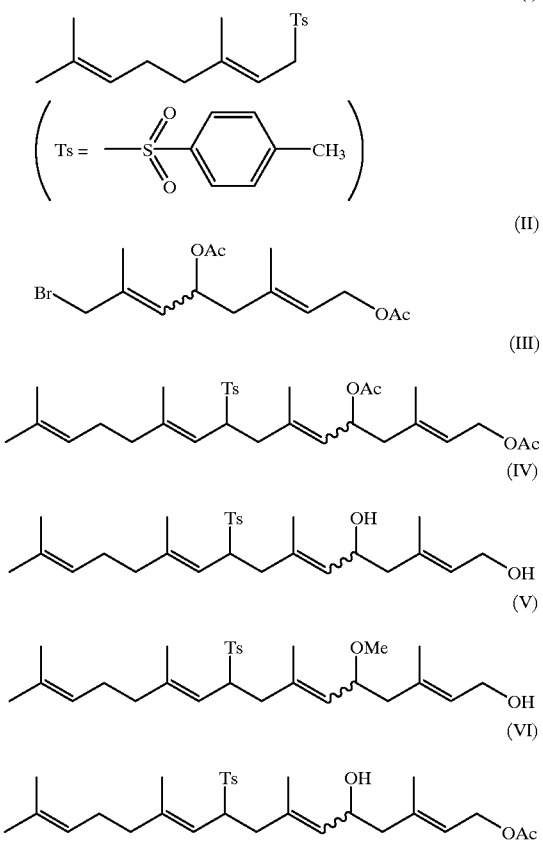

Referential Example 1

In 100 ml of n-hexane was dissolved 40 g (0.204 mol) of geranyl acetate, and 17.1 g (0.071 mol) of trichloroisocyanuric acid was added slowly and maintained between −10° C. to 0° C. for six hours. After the reaction, excessive trichloroisocyanuric acid and by-produced isocyanuric acid were removed by filtration. The filtrate was washed with an aqueous sodium hydrogencarbonate solution and water, dried over anhydrous magnesium sulfate, and the solvent was evaporated to yield a crude product. The crude product obtained was purified by silica gel chromatography to provide 6-chloro-3,7-dimethyl-2,7-octadiene-1-acetate (hereinafter, compound (a)) in a yield of 86% in the form of pale yellow oil.

$^1$H-NMR δ (CDCl$_3$) 1.71 (3H, s), 1.81 (3H, s), 1.90–2.22 (4H, m), 2.05 (3H, s), 4.34 (1H, t, J=7 Hz), 4.59 (2H, d, J=7 Hz), 4.90 (1H, s), 5.01 (1H, s), 5.37 (1H, t, J=7 Hz).

Referential Example 2

Into a dry four-neck flask, 6.8 g (0.17 mol) of sodium hydroxide fine powder, 2.2 g (8.5 mmol) of triphenylphosphine, 1.4 g (5.1 mmol) of tetra-n-butylammonium chloride, 0.62 g (1.7 mmol of allylpalladium chloride dimer and 100 ml of THF were charged. To the mixture was added dropwise a solution (150 ml) of 40 g (0.17 mol) of the compound (a) in THF at room temperature over one hour under stirring. After stirring at room temperature for three days, the reaction mixture was quenched with water, and extracted with ether. The organic layer obtained was washed with a saturated brine, dried over anhydrous magnesium sulfate, and the solvent was evaporated to yield a crude product. The resulting crude product was purified by silica gel chromatography to provide 3,7-dimethyl-2,5,7-octatriene-1-acetate (hereinafter, compound (b)) in a yield of 65%.

$^1$H-NMR δ (CDCl$_3$) 1.70 (3H, s), 1.85 (3H, s), 2.08 (3H, s), 2.81 (2H, d, J=7 Hz), 4.58 (2H, d J=7 Hz), 4.90 (2H, s), 5.37 (1H, t, J=7 Hz), 5.61 (1H, td, J=7, 16 Hz), 6.16 (1H, d, J=16 Hz)

Referential Example 3

20.1 g (0.1 mol) of the compound (b) and 100 ml of acetic acid were charged, and 18.3 g (0.1 mol) of N-bromosuccinimide was added slowly at room temperature. The reaction mass became uniform in 10 to 15 minutes at room temperature. After stirring for two hours, the mixture was quenched with water, and extracted with toluene. The organic layer obtained was dried over anhydrous magnesium sulfate, and the solvent was evaporated to yield an about 1:1 mixture of 8-bromo-3,7-dimethyl-2,6-octadiene-1,5-diacetate (hereinafter, compound (c) (mixture of E, Z isomers)) and 8-bromo-3,7-dimethyl-2,5-octadiene- 1,7-diacetate (hereinafter, compound (d) (mixture of E, Z isomers)) in a yield of 95%. The mixture obtained was separated and purified to provide the compounds (c) and (d) each in the form of pale yellow oil.

Compound (c)

$^1$H-NMR δ (CDCl$_3$) 1.77 (3H, s), 1.82 (3H, s), 1.98 (3H, s), 2.02 (3H, s), 2.19 (2H, m), 3.89 (2H, s), 4.55 (2H, d, J=7 Hz), 5.37 (1H, t, J=7 Hz), 5.48–5.62 (2H, m)

Compound (d)

$^1$H-NMR δ (CDCl$_3$) 1.65 (3H, s), 1.68 (3H, s), 2.05 (3H, s), 2.06 (3H, s), 2.78 (2H, d, J=6 Hz), 3.67 (1H, d, J=11 Hz), 3.82 (1H, d, J=11 Hz), 4.57 (2H, d, J=7 Hz), 5.35 (1H, t, J=7 Hz), 5.61–5.77 (2H, m)

The following are the structural formulae of the compounds (a)–(d) of the Referential Examples.

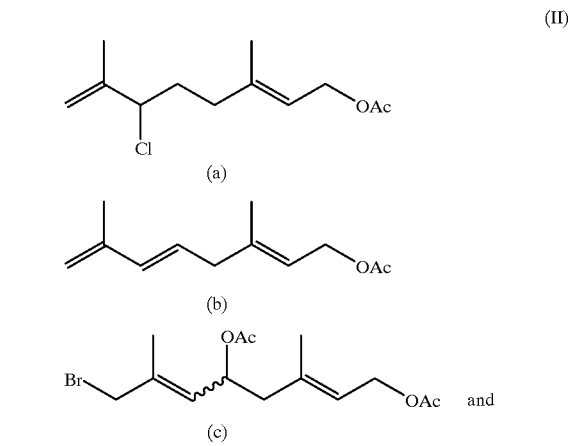

-continued

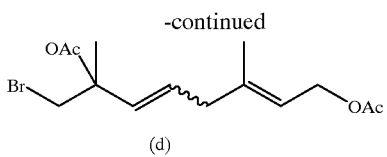

(d)

What is claimed is:

1. A tetraene derivative of the formula (1):

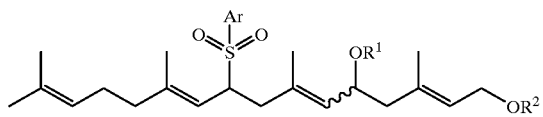

(1)

wherein Ar represents an aryl group which may be optionally substituted with at least one substituent, and $R^1$ and $R^2$ are identical or different and represent a hydrogen atom, a lower alkyl group or a protective group of a hydroxyl group.

2. The tetraene derivative according to claim 1, wherein the protective group of a hydroxyl group is an acetyl group.

3. A process for producing a tetraene derivative of the formula (4):

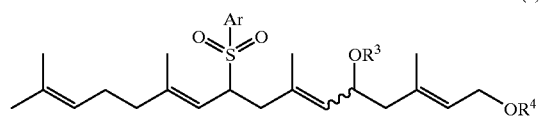

(4)

wherein Ar represents an aryl group which may be optionally substituted with a substituent and $R^3$ and $R^4$ are the same or different and represent a protective group of a hydroxyl group, the process comprising reacting a sulfone of the formula (2):

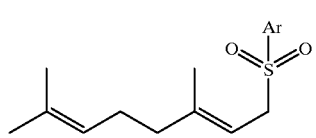

(2)

wherein Ar has the same meaning as defined above, with a halohydrin derivative of the formula (3):

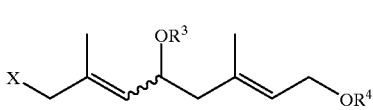

(3)

wherein X represents a halogen atom, and $R^3$ and $R^4$ has the same meaning as defined above, in the presence of a base.

4. A process for producing a tetraene derivative of the formula (5):

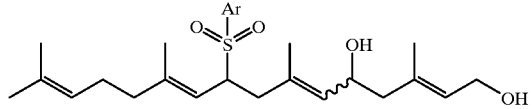

(5)

wherein Ar represents an aryl group which may be optionally substituted with at least one substituent, the process comprising subjecting the tetraene derivative of the following formula (4) to a deprotection reaction,

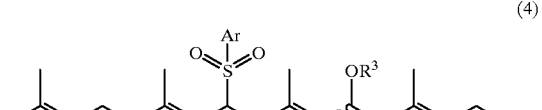

(4)

wherein Ar represents an aryl group which may be optionally substituted with a substituent, and $R^3$ and $R^4$ are the same or different and represent a protective group of a hydroxyl group.

5. A process for producing a tetraene derivative of the formula (6):

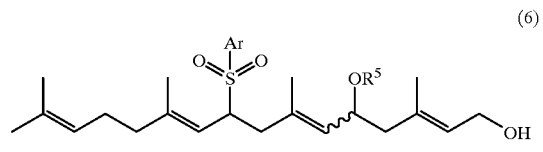

(6)

wherein Ar represents an aryl group which may be optionally substituted with at least one substituent, and $R^5$ represents a lower alkyl group, the process comprising reacting the tetraene derivative of the following formula (5) with a lower alcohol in the presence of an acid catalyst,

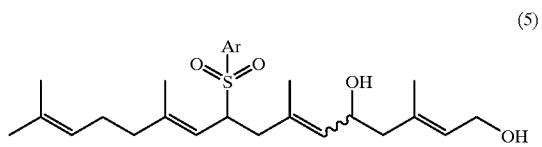

(5)

wherein Ar represents an aryl group which may be optionally substituted with a substituent.

6. A process for producing a tetraene derivative of the formula (7):

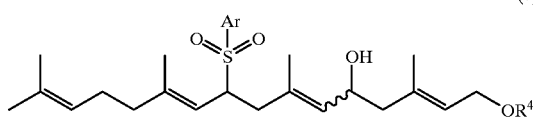

(7)

wherein Ar represents an aryl group which may be optionally substituted with at least one substituent, and $R^4$ represent a protective group of a hydroxyl group, the process comprising reacting a tetraene derivative of the following formula (5) with a protective agent in the presence of a phase-transfer catalyst and a base,

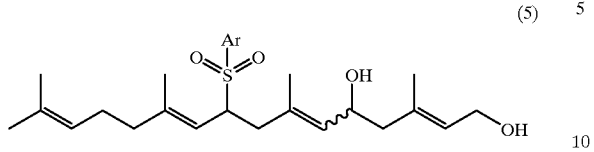
(5)

wherein Ar represents an aryl group which may be optionally substituted with at least one substituent.

7. The process according to claim 6, wherein the protective agent is acetyl chloride or acetic anhydride.

8. The process according to claim 7, wherein the base is an inorganic base.

9. The process according to claim 8, wherein the inorganic base is a hydroxide of an alkali metal, a hydroxide of an alkaline earth metal, a carbonate of an alkali metal, a carbonate of an alkaline earth metal, a hydrogencarbonate of an alkali metal or a hydrogencarbonate of an alkaline earth metal.

10. The process according to claim 5, wherein the tetraene derivative of the formula (5) is obtained by a process that comprises subjecting a tetraene derivative of the following formula (4) to a deprotection reaction,

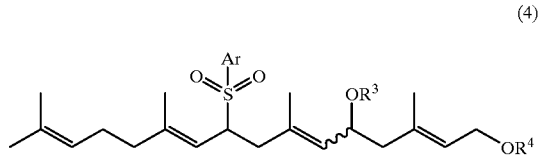
(4)

wherein Ar has the same meaning as defined above, and $R^3$ and $R^4$ are the same or different and represent a protective group of a hydroxyl group.

11. The process according to claim 10, wherein the tetraene derivative (4) is obtained by a process that comprises reacting a sulfone of the formula (2):

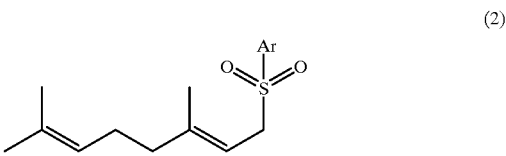
(2)

wherein Ar has the same meaning as defined above, with a halohydrin derivative of the formula (3):

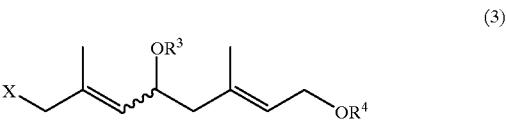
(3)

wherein X represents a halogen atom, and $R^3$ and $R^4$ has the same meaning as defined above, in the presence of a base.

12. The process according to claim 3, wherein the base used is an alkyllithium, a Grignard reagent, an alkali metal hydroxide, an alkaline earth metal hydroxide, an alkali metal hydride, an alkaline earth metal hydride, an alkali metal alkoxide, and an alkaline earth metal alkoxide.

13. The process according to claim 11, wherein the base used is an alkyllithium, a Grignard reagent, an alkali metal hydroxide, an alkaline earth metal hydroxide, an alkali metal hydride, an alkaline earth metal hydride, an alkali metal alkoxide, and an alkaline earth metal alkoxide.

14. The process according to claim 5, wherein the lower alcohol is methanol, ethanol or isopropanol.

15. The process according to claim 10, wherein the lower alcohol is methanol, ethanol or isopropanol.

16. The process according to claim 11, wherein the lower alcohol is methanol, ethanol or isopropanol.

\* \* \* \* \*